United States Patent [19]

Koestler et al.

[11] Patent Number: 5,520,881

[45] Date of Patent: May 28, 1996

[54] ANOXIC TREATMENT METHOD AND APPARATUS

[75] Inventors: Robert J. Koestler, Hasbrouck Heights, N.J.; Richard Sheryll, New York; William Louche, Tappan, both of N.Y.

[73] Assignee: Art Care International, Inc., Orangeburg, N.Y.

[21] Appl. No.: 350,538

[22] Filed: Dec. 7, 1994

[51] Int. Cl.[6] .............................. A61L 2/00; G01N 21/00
[52] U.S. Cl. .................................. 422/3; 422/1; 422/37; 422/40; 422/62; 422/83; 422/292; 435/31
[58] Field of Search ........................ 422/1, 3, 28, 32, 422/37, 40, 62, 83, 89, 292, 294, 305; 435/31, 32, 291, 296, 311, 313, 807; 356/318

[56] References Cited

U.S. PATENT DOCUMENTS

| | | | |
|---|---|---|---|
| 3,346,464 | 10/1967 | Ernst | 435/31 |
| 3,365,307 | 1/1968 | Dixon | 422/3 X |
| 4,535,586 | 8/1985 | Eberle | 53/432 |
| 4,646,914 | 3/1987 | Gipson | 206/45.34 |
| 4,961,283 | 10/1990 | Forbes | 43/124 |
| 5,108,907 | 4/1992 | Pleass et al. | 435/31 X |
| 5,238,648 | 8/1993 | Kremen | 422/40 |
| 5,260,023 | 11/1993 | Evans, II | 422/40 |
| 5,326,543 | 7/1994 | Fiorenzano, Jr. | 422/32 |
| 5,360,593 | 11/1994 | Bapatta | 422/1 X |
| 5,416,002 | 5/1995 | Steele et al. | 435/31 X |

Primary Examiner—Robert J. Warden
Assistant Examiner—Krisanne M. Thornton
Attorney, Agent, or Firm—Cobrin Gittes & Samuel

[57] ABSTRACT

An anoxic treatment process which eliminates organisms such as insects, fungi and/or microbes from fine art objects such as paintings includes filling an enclosure placed around the object, flushing the enclosure of oxygen by applying an inert gas such as argon, and/or helium separately or in combination, and maintaining selected conditions of pressure, temperature, humidity and ph (acidity) for a selected period of time, typically on the order of several weeks. In one practice of the invention, infrared spectra are monitored to determine when all live organisms have been eliminated from the object, by measuring respiratory by-products from the organisms to determine when all have been eliminated. The by-product measurement system may utilize a Fourier Transform Infrared Spectroscopy system (FTIR) to monitor carbon dioxide and/or methane.

17 Claims, 10 Drawing Sheets

ANOXIC TREATMENT METHOD AND APPARATUS

BACKGROUND OF THE INVENTION

This invention relates generally to systems for fumigation, and, more particularly, relates to apparatus and methods for anoxic control of insects, fungi, and other undesirable biological organisms in or on fine art objects.

Within the museum environment, numerous objects of fine art are subject to attack and degradation by insects, fungi and other organisms. The realization of the need for control of such organisms often arises only after visible damage has resulted from infestation, at which point museum personnel often resort to application of commonly-available fumigants. Unfortunately, many such fumigants are likely to damage the art object even as they control the biological organisms. Prior art fumigation and/or insect control is described in the following documents/publications:

Koestler, et al., "*Application of Anoxic Treatment for Insect Control in Manuscripts of the Library of Megisti Laura, Mount Athos, Greece*", The Metropolitan Museum of Art, New York, USA, New York University, Institute of Fine Arts, New York, USA, ARSAG Meeting, Paris, 1994;

Reichmuth et al., "*Nitrogen-Flow Fumigation for the Preservation of Wood, Textiles, and Other Organic Material From Insect Damage, Proc. Int. Conf. Controlled Atmosphere and Fumigation in Grain Storages*", Winnipeg, Canada, Jun. 1992, Caspit Press Ltd. Jerusalem, pp. 121–128, Navarro, Donahaye, eds.;

Koestler, "*Practical Application of Nitrogen and Argon Fumigation Procedures for Insect Control in Museum Objects*", 2nd International Conference on Biodeterioration of Cultural Property, Yokohama, Japan, Oct. 5–8, 1992;

Koestler, et al., "*Visual Effects of Selected Biocides on Easel Painting Materials,*" Studies in Conservation, Journal of the International Institute for Conservation of Historic and Artistic Works, London, England, 1992/1993; and Koestler, "*Insect Eradication Using Controlled Atmospheres and FTIR Measurement for Insect Activity,*" ICOM Committee for Conservation, 1993;

The publication by Koestler entitled "*Practical Application . . . *" discloses the need for controlling insect infestations, and the use of a low-oxygen atmosphere, specifically, the use of argon, nitrogen, or helium, to flush out the existing oxygen level found in air and thereby eliminate insects from art objects. The paper discusses the humidity, temperature, pressure, and time parameters to be employed, and provides examples of rigid and flexible container systems.

The publication by Koestler entitled "Insect Eradication . . ." alludes to the use of FTIR analysis to detect the presence or absence of insects in artworks.

In addition, various devices and methods for storage and/or fumigation of objects are disclosed in the following United States and foreign patents:

| U.S. Pat. No. | Date | Inventor |
| --- | --- | --- |
| 5,238,648 | 24 August 1993 | Kremen |
| 5,128,160 | 07 July 1992 | Fath |
| 4,927,497 | 22 May 1990 | Sharpe |
| 4,646,914 | 03 March 1987 | Gipson |
| 4,548,824 | 22 October 1985 | Mitchell |
| 4,535,586 | 20 August 1985 | Eberle |
| 4,287,152 | 01 September 1981 | Hoover |
| 4,183,160 | 15 January 1980 | Brodersen |
| 3,943,987 | 16 March 1976 | Rossi |
| 3,409,167 | 24 March 1967 | Blanchard |

| Country | Patent No. | Date |
| --- | --- | --- |
| French | 2,643,232 | 24 August 1990 |
| EPO | 468,545 | 29 January 1992 |

The noted patent to Kremen discloses a hermetic enclosure assembly for preservational storage or display of degradable objects.

Fath discloses a method for preservation of vegetables using nitrogen monoxide or argon with optionally up to 50 percent oxygen.

Sharpe discloses a method of preventing degradation of books, utilizing amine vapors.

Gipson discloses a sealed enclosure for display objects.

Eberle discloses a method of storing agricultural products in a fluid-tight container, and displacing the air in the container with a substitute gas.

Hoover et al. discloses a method for storing developed color photographic film, including evacuating a container and filling the container with an inert gas.

Brodersen discloses an evacuatable mounting element for drawings or paintings.

Rossi discloses a recloseable air-tight container with evacuation elements.

Additionally, U.S. Pat. No. 3,963,927 (Bruce et al.) discloses detection of hidden insects in grain by use of measurement of respired carbon dioxide by an infrared gas analyzer.

The remaining U.S. and foreign patents disclose comparable methods and/or devices.

The foregoing patents and/or publications, however, do not set forth a systematic approach to eradication of undesirable biological organisms (including fungi and other micro-organisms) from fine art objects, particularly an approach which enables precise control, monitoring and reproducibility of the process, such that effectiveness of biological control is optimized while avoiding damage to the art object.

Accordingly, there exists a need for improved fumigation methods and apparatus, particularly a systematic approach which enables precise control and monitoring of the process.

It is accordingly an object of the invention to provide improved fumigation methods and apparatus.

It is another object of the invention to provide such methods and apparatus which are effective against fungi and other micro-organisms, as well as insects.

It is a further object of the invention to provide such methods and apparatus which effectively destroy the undesirable insects, fungi or other biological organisms without harm to the artwork.

Other general and specific objects of the invention will in part be obvious and will in part appear hereinafter.

SUMMARY OF THE INVENTION

The foregoing objects are attained by the invention, which in one aspect provides an anoxic treatment process intended to eliminate organisms such as insects, fungi and/or microbes from fine art objects such as paintings. The process may also be adapted to larger formats, such as the elimination of such organisms from an entire building. The process involves the application of inert gases such as argon and/or helium separately or in combination, to flush an enclosure containing a fine art object such that oxygen and/or air are eliminated from the enclosure and organisms therein are deprived of gases required for metabolic processes. The enclosure may be of rigid construction or flexible walled.

In one aspect thereof, the process of eliminating biological organisms from an object includes the steps of surrounding the object with a sealable container, filling the container with an inert gas such as argon to displace the oxygen and/or air, sealing the container, and maintaining selected conditions of pressure, temperature and humidity for a selected period of time, typically on the order of several weeks, until the organisms are eliminated. In one practice of the invention, the object is first tested prior to application of the inert gas, to determine whether infestation exists. If visible infestation of the art object is present, the inert gas treatment phase will be implemented first, without need for the initial testing phase. In addition, testing will be implemented following the inert gas treatment phase, to determine whether all live organisms have been eliminated from the object.

In one practice of the testing phase of the invention, indicia of live organisms are monitored to determined whether such organisms are present. For example, infrared spectra can be monitored to determine whether live organisms are present in the object. The process may employ measurement of respiratory by-products from the insects, fungi or other micro-organisms to determine when all such organisms have been eliminated.

The by-product measurement system may utilize a Fourier Transform Infrared Spectroscopy system (FTIR) or other detection method. The by-products monitored may include carbon dioxide, methane, or other gases generated by metabolic processes. FTIR permits non-contact assessment of respiration activity of insects, fungi, bacteria, algae and other organisms in or on the object to be treated. Activity measurement may also be accomplished by utilization of bio-luminescence techniques. The system can also utilize other activity measurement apparatus in accordance with conventional measurement engineering practice.

Accuracy of testing is enhanced in accordance with the invention by measuring utilizing a "control chamber" in parallel with the "treatment chamber" containing the art object. In one aspect of the invention both the control chamber and the treatment chamber are flushed with air or carbon dioxide-free air (for greater infra-red measurement resolution) having the same pH, temperature and humidity characteristics. FTIR or other equivalent measurements are then performed on the contents of both chambers. In this manner, errors can be reduced or eliminated from the measurement and testing phase.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and the accompanying drawings, in which.

DESCRIPTION OF ILLUSTRATED EMBODIMENTS

The drawing figures herewith depict apparatus which provides an anoxic insect treatment process intended to test for and eliminate organisms such as insects, fungi and/or microbes from paintings and other fine art objects. The process may also be adapted to larger formats, such as the elimination of undesirable organisms from an entire building. The drawing figures not only depict the apparatus utilized in accordance with the invention, but also present a chronological sequence of the process of the invention.

One aspect of the process in accordance with the invention involves first testing the art object to determine whether live organisms are present in or on the object. Such testing may employ measurement of respiratory by-products from the insects, fungi and or other micro-organisms to determine when all such organisms have been eliminated. The by-product measurement system may utilize a Fourier Transform Infrared Spectroscopy system (FTIR) or other detection method, in which infrared spectra responsive to metabolic by-products are monitored to determine whether live organisms are present in or on the object. The by-products monitored may include carbon dioxide, methane or other respired gases from organisms. FTIR permits assessment of respiration activity of insect and microbes, including fungi, bacteria, and algae, in or on the art object. Other bio-activity measurement techniques can be utilized, including bio-fluorescence measurements. In addition, solid-state detectors of gases can be utilized. Other known bio-sensors, such as "sniffer chips" sensitive to molecular weight and ceramic metallic ("cermet") microsensors that identifies electrical signatures of individual gases can be employed.

Another aspect of the process in accordance with the invention involves the elimination of the undesired organisms from the object to be treated. If visible infestation of the art object is present, this treatment phase will be implemented first, without need for the initial testing phase noted above. The treatment aspect involves the introduction of argon, helium and/or other inert gases, separately or in combination, into a container containing the object, thereby displacing air and/or oxygen from the container and depriving the organisms of gases required for metabolic processes. The container may be of rigid construction or flexible walled.

In particular, the process includes the steps of surrounding an object to be preserved with a sealable container, filling the container with an inert gas such as argon to displace the air and/or oxygen in the container, sealing the oxygen-purged container, and maintaining selected conditions of pressure, temperature and humidity in the container for a selected period of time, typically on the order of several weeks, until the organisms are eliminated. The time constants involved can be adjusted by changing various system parameters, such as relative humidity and other factors.

Determination of whether organisms are eliminated is accomplished through bio-activity measurement as noted above. If the organisms have not been completed eliminated, as indicated by the presence of metabolic by-products, the cycle of treatment with inert gas is repeated.

In summary, the following aspects of the invention are discussed herein:

(i) An iterative treatment cycle for eliminating microbial, fungal, and/or insect infestation utilizing argon and/or other inert gases in combination with selected time, pressure, acidity (pH), and relative humidity (RH) parameters and measurement of biological activity (wherein various forms of activity measurement are employed);

(ii) Apparatus for implementing the above-noted process, including filter elements, control chamber elements for providing baseline measurement, a purge configuration, and laser detection or gas-based bio-activity measurement elements placed within the process chamber; and (iii) Special chambers and/or containers adapted for above-noted process, having porting and/or other physical characteristics which facilitate the implementation of the process.

In general, the following discussion details a process in accordance with the invention for destroying biological organisms within or on an art object, without damage to the art object, by use of an inert gas such as argon within a chamber; subsequent flushing of the chamber by a controlled gas supply; testing for biological activity in conjunction with a "control" chamber; and return to the inert-gas phase if biological activity is detected.

Testing Phase

As noted above, one aspect of the process in accordance with the invention involves first testing the art object to determine whether live organisms are present in or on the object. If visible infestation of the object is present, the treatment phase will be implemented first, without need for the initial testing phase. In the typical case, however, initial testing will be employed.

Figure 1:
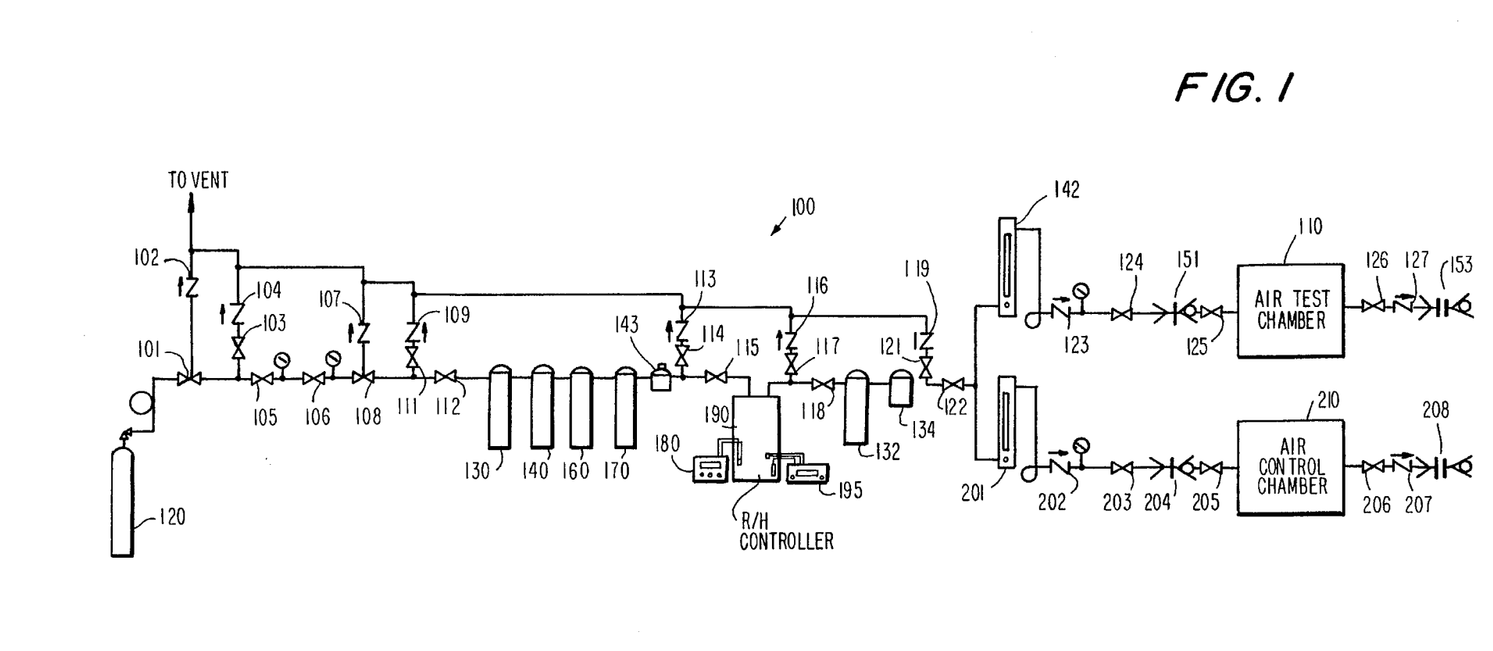
FIG. 1 is a schematic diagram depicting apparatus in accordance with the invention including a treatment chamber and a control chamber for implementing the bio-activity testing phase of the invention.

FIG. 1 is a schematic diagram depicting apparatus in accordance with the invention including a "treatment chamber" and a "control chamber" for initializing the bio-activity testing phase of the invention. In order to accurately test for the presence of biological activity in or on the object to be treated, it is preferable to utilize a control chamber in tandem with the treatment chamber, so as to enable the cancellation of errors due to contaminants or other gas constituents. The apparatus of FIG. 1 enables the use of an "air flush and fill cycle" which ensures that both the treatment chamber and the control chamber are flushed with the same quality and constituents of air (preferably carbon dioxide-free air) prior to measurement of gases produced by living organisms.

The apparatus 100 shown in FIG. 1 includes treatment chamber 110 into which the object is placed, gas source 120 (preferably providing carbon dioxide-free air), filters 130, 132, 134, 140, traps 160, 170, temperature controller 180, relative humidity controller 190, and pH controller 195. The temperature, humidity and pH controllers are of conventional design and construction. The apparatus can also include check valves 102, 104, 107, 109, 113, 116, 119, 123, 127, 202, and 207; pressure relief valves 101 and 108; pressure regulator 106 and isolation valves 103, 105, 111, 112, 114, 115, 117, 118, 121, 122, 124-126, 203, 205, and 206 all situated at various locations throughout the system in accordance with conventional engineering practice. Still further, the apparatus can include flow meters 142, 201 and a moisture and impurity indicator 143 or other types of indicating filters which indicate when they need to be changed. Pressure gauges 129 can also be utilized throughout the system to enable pressure monitoring.

The system also includes quick-disconnect elements 151, 153, 204, 208, which enable the treatment and control chambers to be removed from the feed lines while in a sealed condition, for testing and other processes, as described herein. Those skilled in the art will appreciate that conventional spring-loaded quick-disconnect elements can be utilized which automatically seal off when a mating fitting is removed.

The system of FIG. 1 can employ conventional connections for the gas source, conventional industrial pressure regulation apparatus, air bleed-off lines, and conventional filters which remove trace amounts of gases and particulate matter which may be released by the gas supply cylinder(s).

Carbon dioxide trap 160 is used when it is desirable to employ carbon dioxide-free air. Carbon dioxide-free air provides the advantage of eliminating one constituent from infra-red (IR) testing described herein, thereby providing faster and more accurate test results.

The system can further utilize standard flow meters for the chamber gas supply. The conditioning system 180, 190, 195 sets and regulates the temperature, relative humidity (RH) and pH of the gas before it enters the chambers. Control of humidity is often essential during processing of fragile objects, which may be subject to cracking under excessive dryness.

The "control chamber" 210 has associated therewith various conventional control elements including flow meter 201, quick disconnects 204 and 208, and valves 202, 203, 205, 206, 207. The system of FIG. 1 thus utilizes two chambers and a compressed air cylinder or other supply (having appropriate filters in accordance with known engineering practice) for providing a source of air for flushing and filling the chambers.

Figure 2:
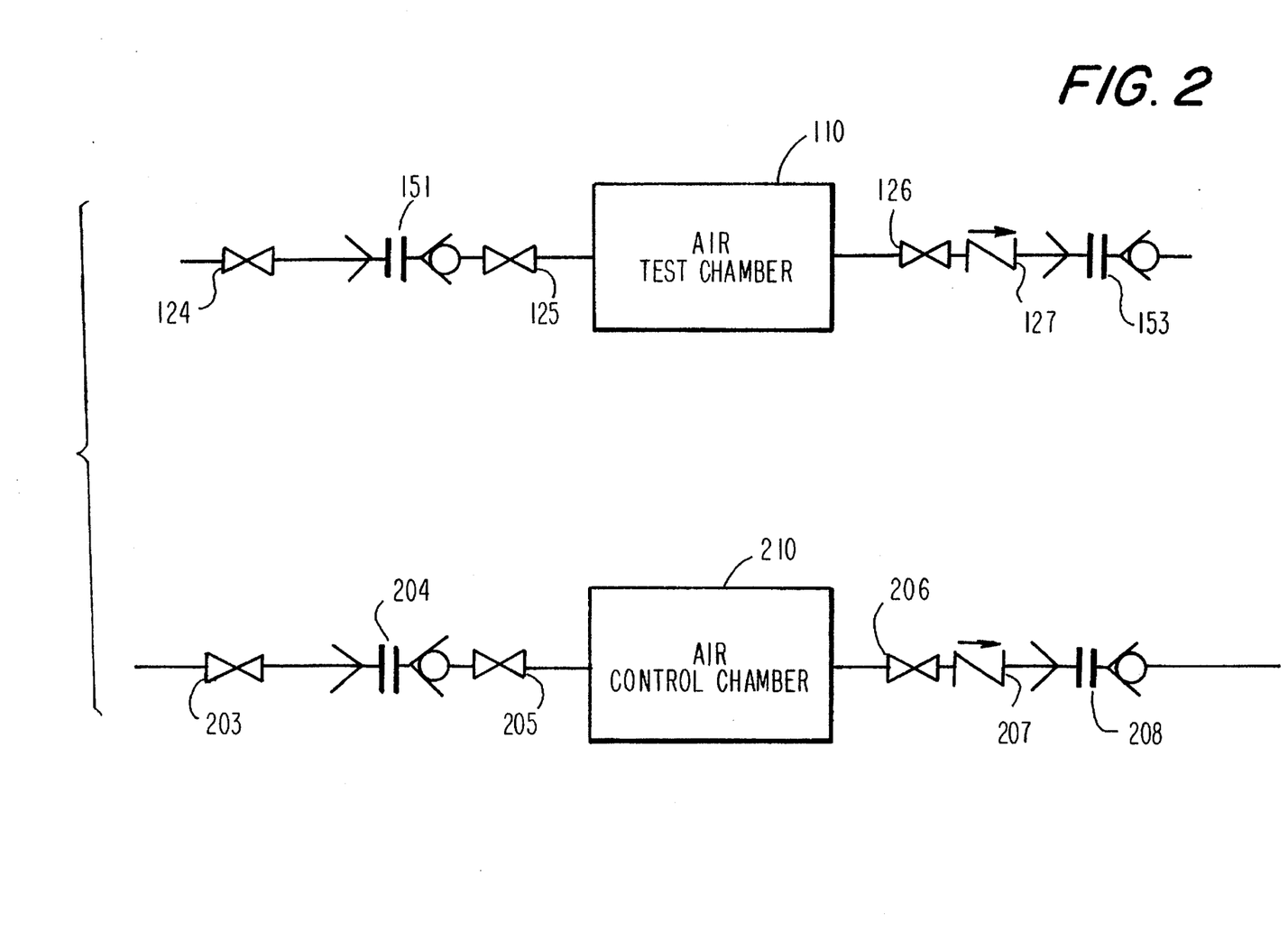
FIG. 2 is a schematic diagram depicting the treatment chamber and control chamber, respectively, prior to connection of a carbon dioxide bio-activity measuring device (quick-disconnect elements disconnected)
Figure 5:
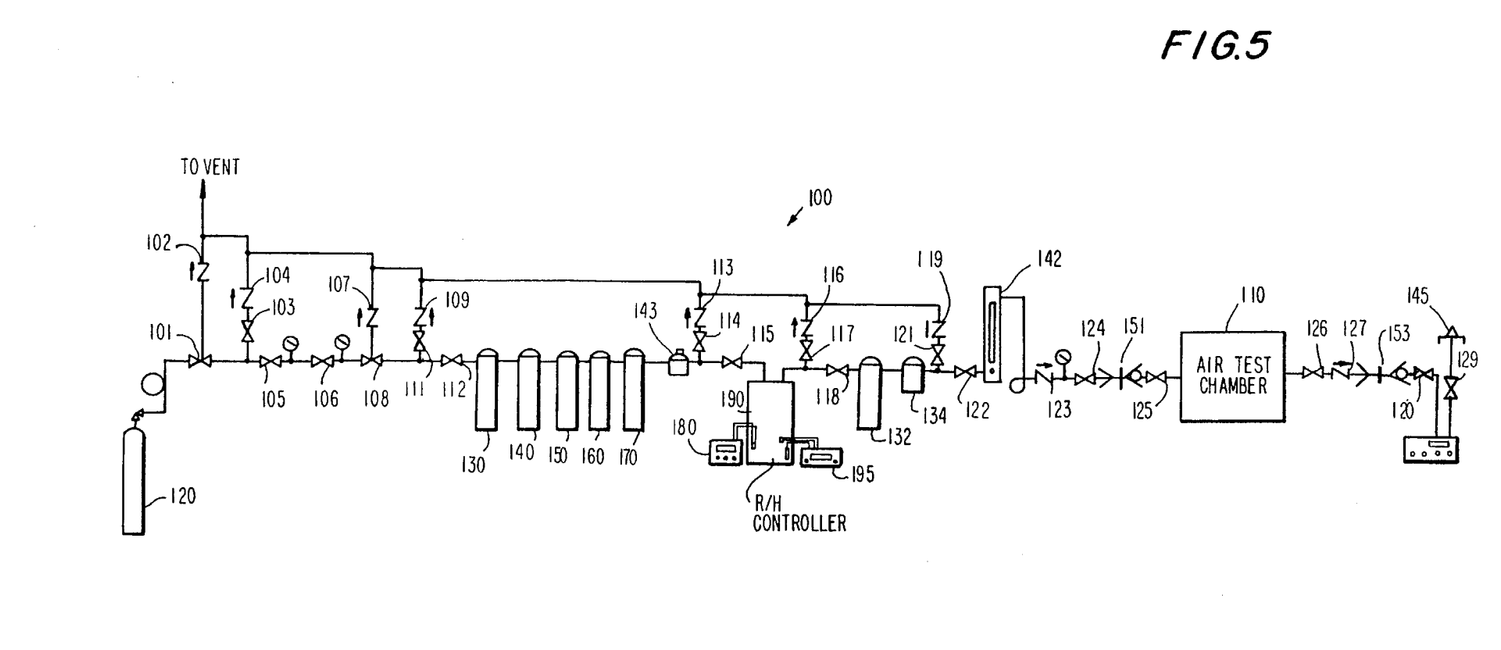
FIG. 5 depicts the apparatus of FIG. 1 with additional components, including a supply of inert gas, for implementing the inert gas treatment phase of the invention.

In operation, compressed air from the air cylinder 120 (or other supply having appropriate filters in accordance with known engineering practice) is allowed to propagate through the system 100 and fill the treatment and control chambers 110 and 210, such that the process chamber 110 (still containing the object under treatment) and the control chamber are filled from the same air source. Then, as shown in FIG. 2, the treatment chamber and the control chamber are separated from the rest of the system 100, by disconnecting the quick-disconnect elements 151 and 204. The system can include an oxygen gas analyzer 144, and an outlet to the atmosphere 313 (FIGS. 2, 3) or 145 (FIG. 5). This combination of oxygen gas analyzer 144, and outlet to the atmosphere 145 may be utilized in FIG. 1 after the assessment of the effective treatment to determine when the proper oxygen level is reached or it can be used in FIG. 5 as discussed hereinafter.

Those skilled in the art will appreciate that the elements of FIG. 1 can be controlled by a suitable computer controller, such as a conventional personal computer (PC) and interface.

Bio-Activity Measurement

Figure 3:
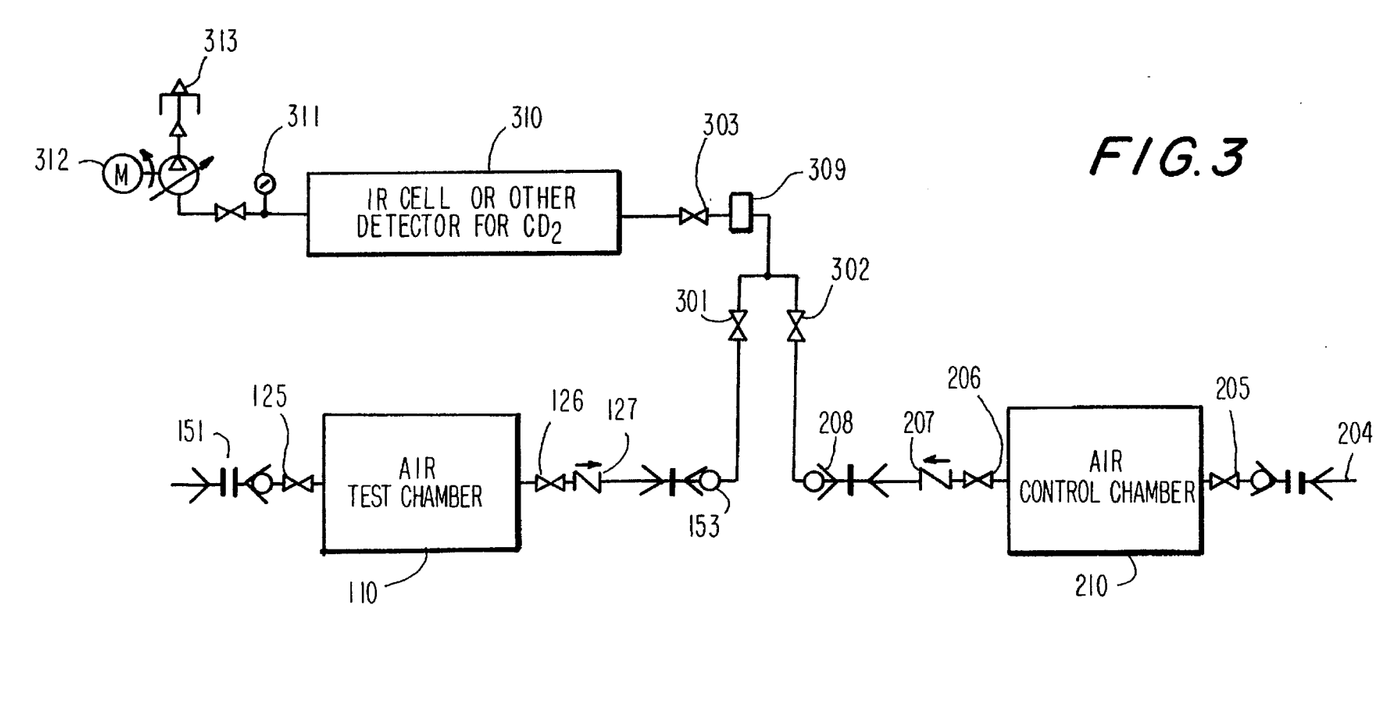
FIG. 3 is a schematic diagram depicting the treatment chamber and control chamber connected to an IR cell or other device for detecting carbon dioxide or other gaseous metabolic product (quick-disconnect elements connected only between the IR cell and respective chambers)

After the preceding phases of processing have been completed, the object to be treated can be tested to determine whether biological organisms are present, and to what extent such organisms are present. In accordance with one practice of the invention, activity measurement is implemented by measuring gases produced by living organisms as a result of metabolic processes, including, but not limited to, production of carbon dioxide or methane. FIG. 3 depicts the treatment chamber and control chamber connected to an IR cell or equivalent device for detecting carbon dioxide or other gaseous metabolic product. In particular, the quick-disconnect elements are shown connected only between the IR cell and respective chamber. The chambers are thus connected to a specialized measuring device for measuring gases indicative of metabolic processes which may occur in biological organisms within the object in the process chamber 110. By way of example, FIG. 3 depicts an infrared cell for measurement of carbon dioxide. Those skilled in the art will appreciate that other measurement devices sensitive to other constituents can also be utilized in accordance with known measurement engineering practice.

As shown in FIG. 3, samples of air are taken from the control chamber and compared to the air taken from the treatment chamber. This is accomplished by actuating valves 301, 302, 303. (A sub-micron filter 309 is utilized to prevent infiltration of spores or similar small particulates. Such a filter can trap spores which may have formed. An ionization filter 311 can be employed (FIGS. 7–10) to precipitate out any fungal spores which have formed.) The measurement device compares the relative levels of carbon dioxide or other selected gas or gases in the two chambers and determines the difference therebetween. If the difference exceeds a predetermined threshold, this indicates the presence of biological activity in the object within the treatment chamber. If respiration by-products from living organisms are detected, then the treatment chamber containing the object to be treated is again connected to the inert gas feed line for filling with inert gas.

Thus, as noted, the detection system may utilize a Fourier Transform Infrared Spectroscopy system (FTIR) or other detection methods. The by-products monitored may include carbon dioxide, methane, and/or other respired gases from organisms. FTIR permits assessment of respiration activity of insect and microbes, including fungi, bacteria, and algae, in or on the art object. Activity measurement may also be accomplished by utilization of bio-luminescence techniques. The system can also utilize other activity measurement apparatus in accordance with conventional measurement engineering practice, such as a gas chromatograph (GC) system. In addition, the FTIR measurement can be implemented by utilizing a laser light source 900 within the process chamber itself FIG. 6. Placing the laser source within the process chamber in conjunction with suitably-located mirror elements 901 to increase the path length of the laser light will substantially improve test resolution. This is because when so configured, the laser light will pass through substantially the entire chamber at least once (and even multiple times if a "folded" light path is provided), such that the path along which the laser can hit carbon dioxide or other molecules of interest is much longer. Placing the laser within the chamber also eliminates the need for disconnecting the process chamber.

Figure 4:
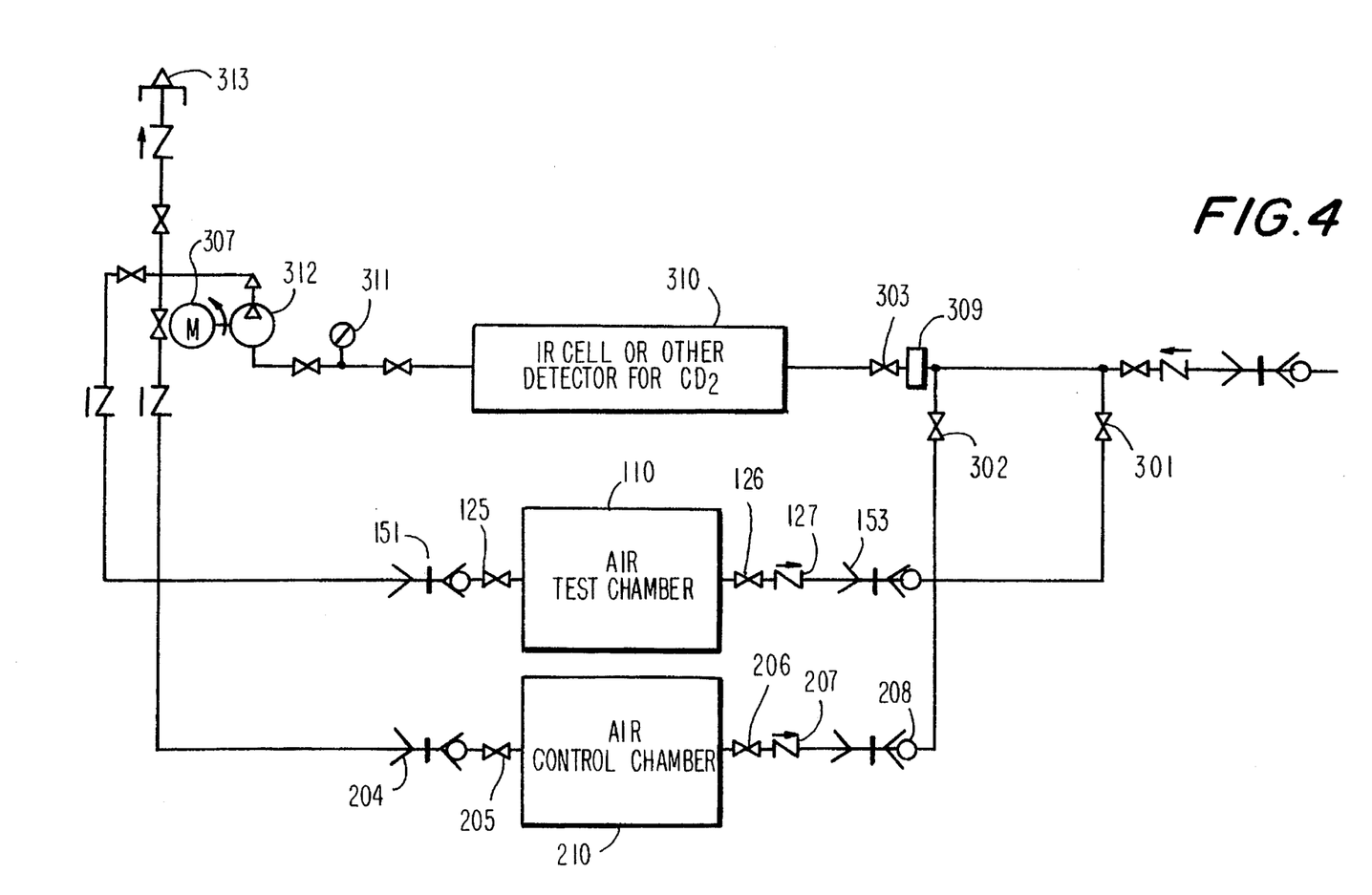
FIG. 4 depicts the treatment chamber and control chamber connected to pump apparatus for recycling the air supplied to the chambers (quick-disconnect elements connected only between the IR cell and respective chambers)

In one practice of the invention, shown in FIG. 4, the air in the system (preferably carbon dioxide-free air, which increases FTIR test resolution and accuracy) is recycled by means of the pump and conduit apparatus shown. FIG. 4 depicts the treatment chamber and control chamber connected to vacuum pump 312 and motor 307 for recycling the air supplied to the chambers, wherein the quick-disconnect elements 153 and 208 between the IR cell and respective chambers are connected to allow passage of gas between the chambers and the testing element 310, and quick-disconnect elements 151 and 204 are also connected to permit recycling of the gas.

Inert Gas Treatment Phase

If the testing phase indicates that biological organisms are present in or on the object to be treated, the treatment chamber is connected as shown in FIG. 5 for inert gas anoxic treatment. As shown in FIG. 5, a source 120 of inert, anoxic gas is activated and the inert gas propagates through the control system such that the treatment chamber 110 is filled with the inert gas. Oxygen and/or air in the treatment chamber 110 are thus displaced by the inert gas. Since the atmosphere in the chamber is anoxic, oxygen-requiring organisms in or on the object to be treated are gradually eliminated. The object is typically left in the anoxic atmosphere in the chamber for a matter of weeks, as determined by testing in accordance with the invention, and then removed for testing as discussed herein. If testing continues to indicate the presence of organisms, then the chamber is reconnected for further inert gas treatment.

As shown in FIG. 5, oxygen monitoring system 144 can be connected to the outlet flow to determine when the proper anoxic level has been reached.

In accordance with one practice of the invention, the inert gas utilized is argon. The choice of argon over nitrogen, currently the most commonly utilized gas for use in controlled atmosphere treatments, is based upon the following factors:

argon is entirely inert;

unlike nitrogen, no evidence has been adduced to indicate the existence of any organisms which can metabolize argon;

argon provides faster "kill rates" than nitrogen (25–50% faster);

if humidity levels rise during treatment, argon will not encourage the development of anaerobic microorganisms; and argon has a higher density than oxygen, and thus it will preferentially sink to the bottom of an enclosure, thereby displacing the oxygen and producing lower oxygen environments over time and providing a location where the art object can be placed.

The procedure may utilize pressurized cylinders or tanker cars of liquefied argon gas. In either case, the procedure uses industry standard pressure regulation, air bleed-off lines and standard filters to remove trace amounts of gases and particulate matter from the cylinder of gases. A conditioning system sets the temperature, relative humidity (RH) and pH of the gas before it enters the process chamber. The flow meter 142 shown in FIG. 5 can be a conventional flow meter which permits regulation of the flow of gas by the system operator or by computer control to ensure that no damage occurs to the object within the enclosure system, particularly when the object is of great age and fragility. In addition, protection of the object against excessive pressure changes is provided by pressure relief valves 101, 108, one actuated by excessively high pressure, and one for low pressure.

Figure 6:
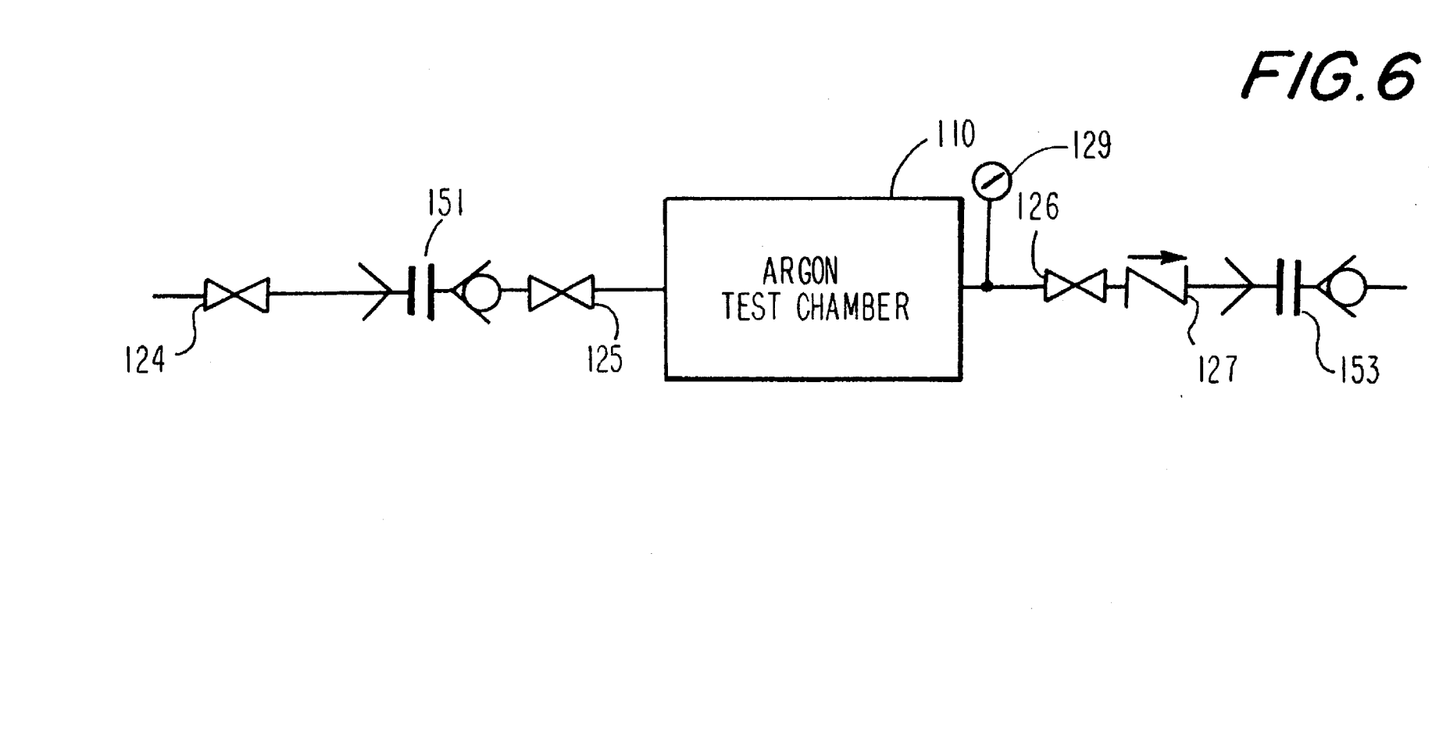
FIG. 6 depicts the treatment chamber housing the art object to be treated in a "stand-alone" configuration, disconnected from the apparatus of FIG. 5, wherein the object is maintained in the inert gas atmosphere in the chamber for a predetermined length of treatment time (quick-disconnect elements disconnected)

In accordance with the invention, after the process chamber is filled with the inert gas, the process chamber will remain disconnected from the feed lines for the duration of the treatment. This state is shown in FIG. 6. In particular, FIG. 6 depicts the treatment chamber 110 filled with inert gas in a "stand-alone" configuration, disconnected from the apparatus of FIG. 5, wherein the object is maintained in the inert gas atmosphere in the chamber for a predetermined length of treatment time. The quick-disconnect elements 151, 153 are disconnected, such that the chamber 110 of FIG. 6 is sealed.

Thereafter, the chamber can be reconnected briefly to re-flush with argon and/or to measure the anoxic environment. Alternatively, the chamber can be connected to a closed-cycle system as detailed below. The exact procedure utilized can be varied, depending upon a determination by conservation personnel in view of the type of art object, its size and age, and other parameters.

Purging and Conditioning

Under certain circumstances it may be necessary to purge the argon test chamber of certain contaminants either in a closed-loop system utilizing an oxygen scrubber or by constant argon feed with dumping of the used gas. Purging may be accomplished in conjunction with known oxygen absorbing materials such as the "Ageless" product marketed by Mitsubishi Gas Company. (See oxygen trap 150 in FIG. 5 and oxygen trap 402 in FIGS. 7–10.) Under other circumstances, as when the container housing the art has a small leak, then apparatus for maintaining equilibrium must be employed. Apparatus for purging and for recovering from leaks is illustrated in FIGS. 7 and 8.

Figure 7:
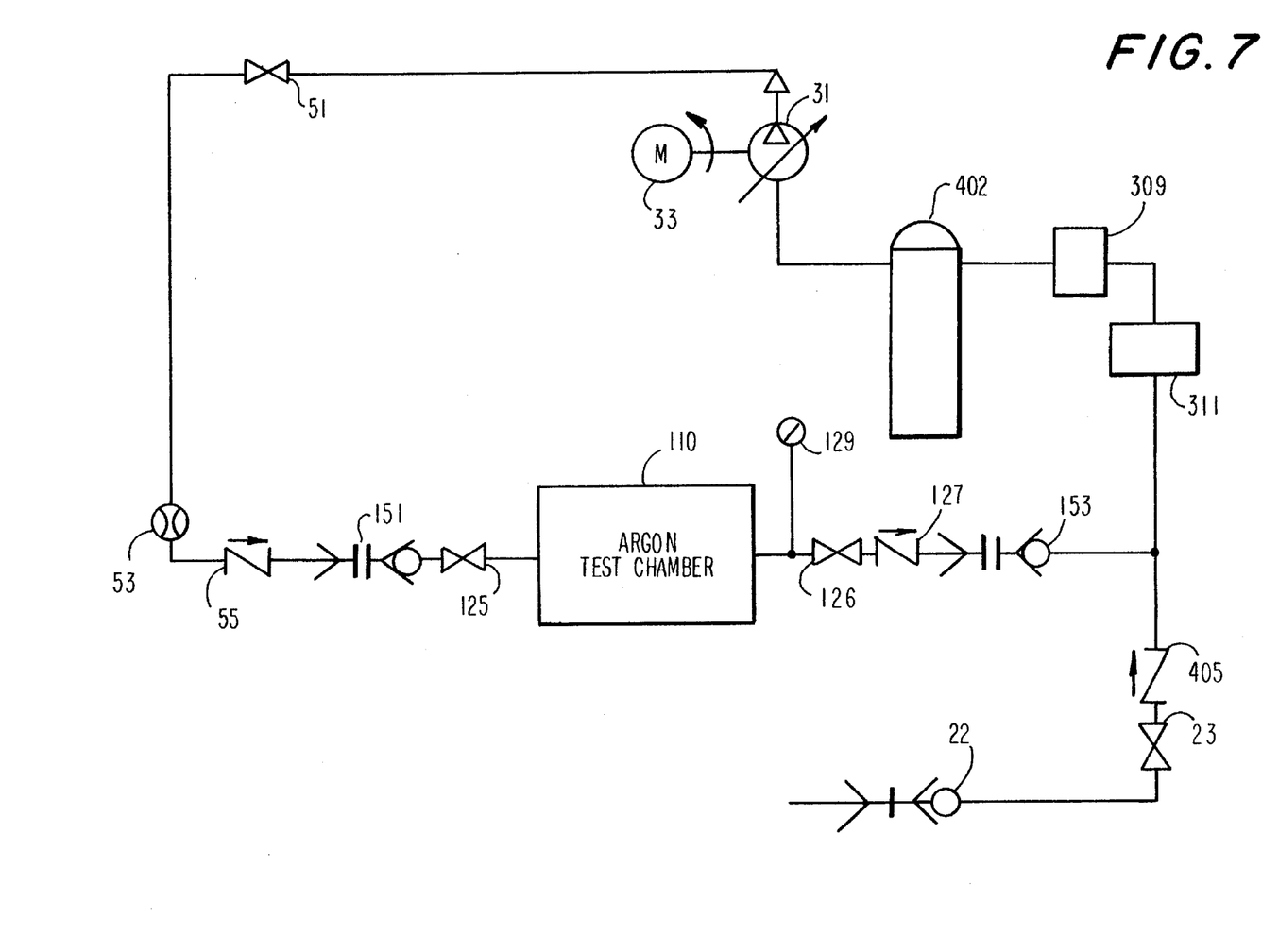
FIG. 7 is a schematic diagram depicting the treatment chamber connected to pump- and oxygen-trap apparatus for purging of lines and components while the inert gas atmosphere in the chamber is maintained for the treatment phase (chamber's quick-disconnect elements disconnected)
Figure 8:
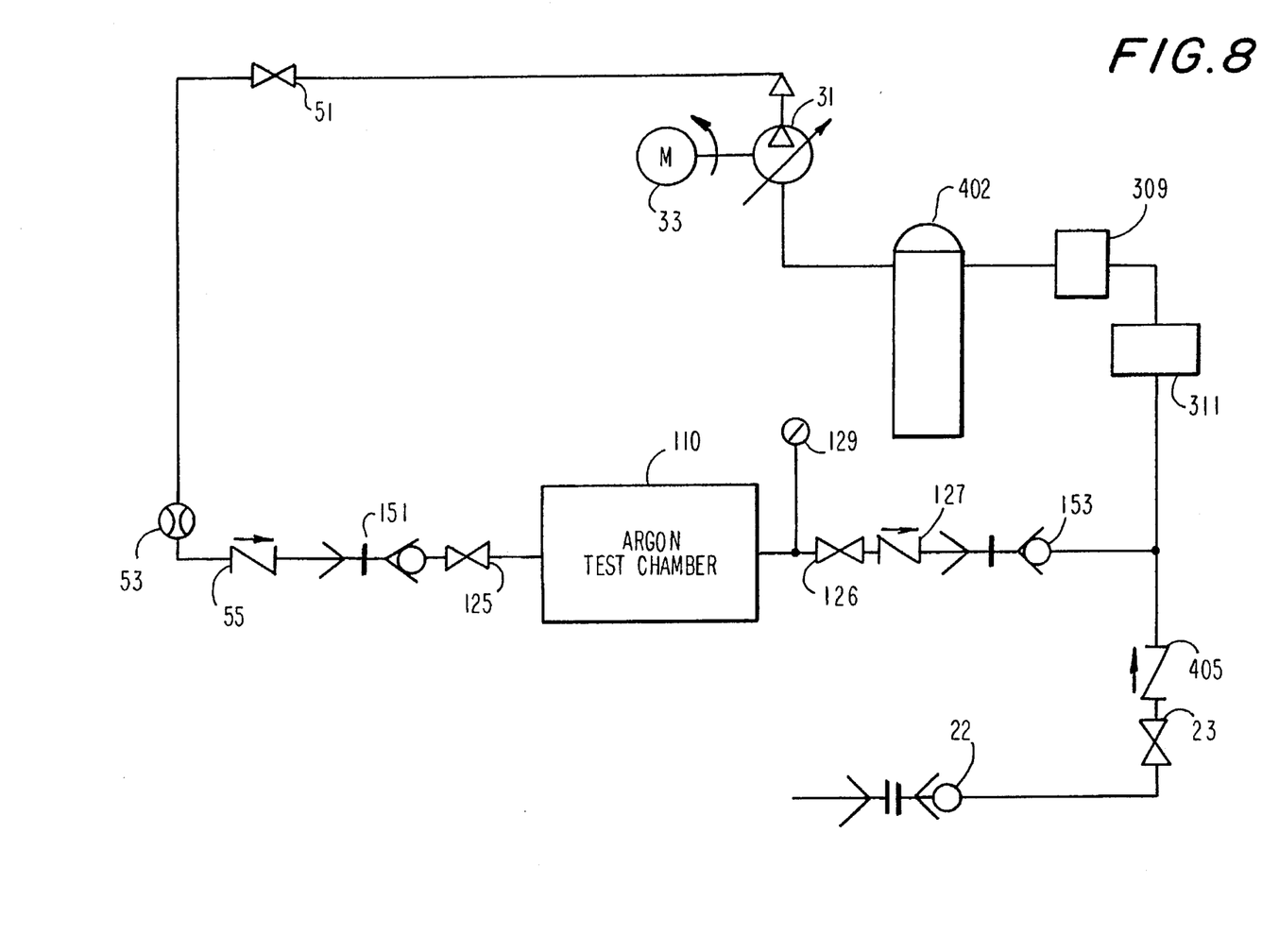
FIG. 8 depicts the treatment chamber apparatus of FIG. 7 connected in a manner to enable recovery from small gas leaks from the chamber (chamber's quick-disconnect elements connected)

FIGS. 7 and 8 are schematic diagrams depicting the treatment chamber 110 connected to pump 31 and motor 33, and oxygen-trap apparatus 402 for scavenging of oxygen while the inert gas atmosphere in the chamber is maintained for the treatment phase. It should be noted that FIG. 7 shows a line-purge configuration while FIG. 8 shows a configuration for treatment and storage of the art object. A flow meter 53 can be utilized to monitor system flow. FIG. 7 also shows that the chamber's quick-disconnect elements 151 and 153 are disconnected for this purging phase. A sub-micron filter 309 can be connected between oxygen trap 402 and quick disconnect 153 to prevent infiltration of spores and other micro-organisms. An ionization filter 311 can also be employed to precipitate out spores.

FIG. 8 depicts the treatment chamber 110 of FIG. 7 connected in a manner to detect and to correct the presence of small gas leaks from the chamber 110. As shown in FIG. 8, the chamber's quick-disconnect elements 151, 153 are connected and in the open state for this leak-check/correct phase. The oxygen trap 402 and gas circulator pump 31 are in-line with the inert gas treatment chamber 110. Ionization filter 311 can also be used to precipitate out spores that may form during this phase. In the configuration of FIG. 8, commercially available sonic leak detectors can be utilized to detect any gas leaks.

Figure 9:
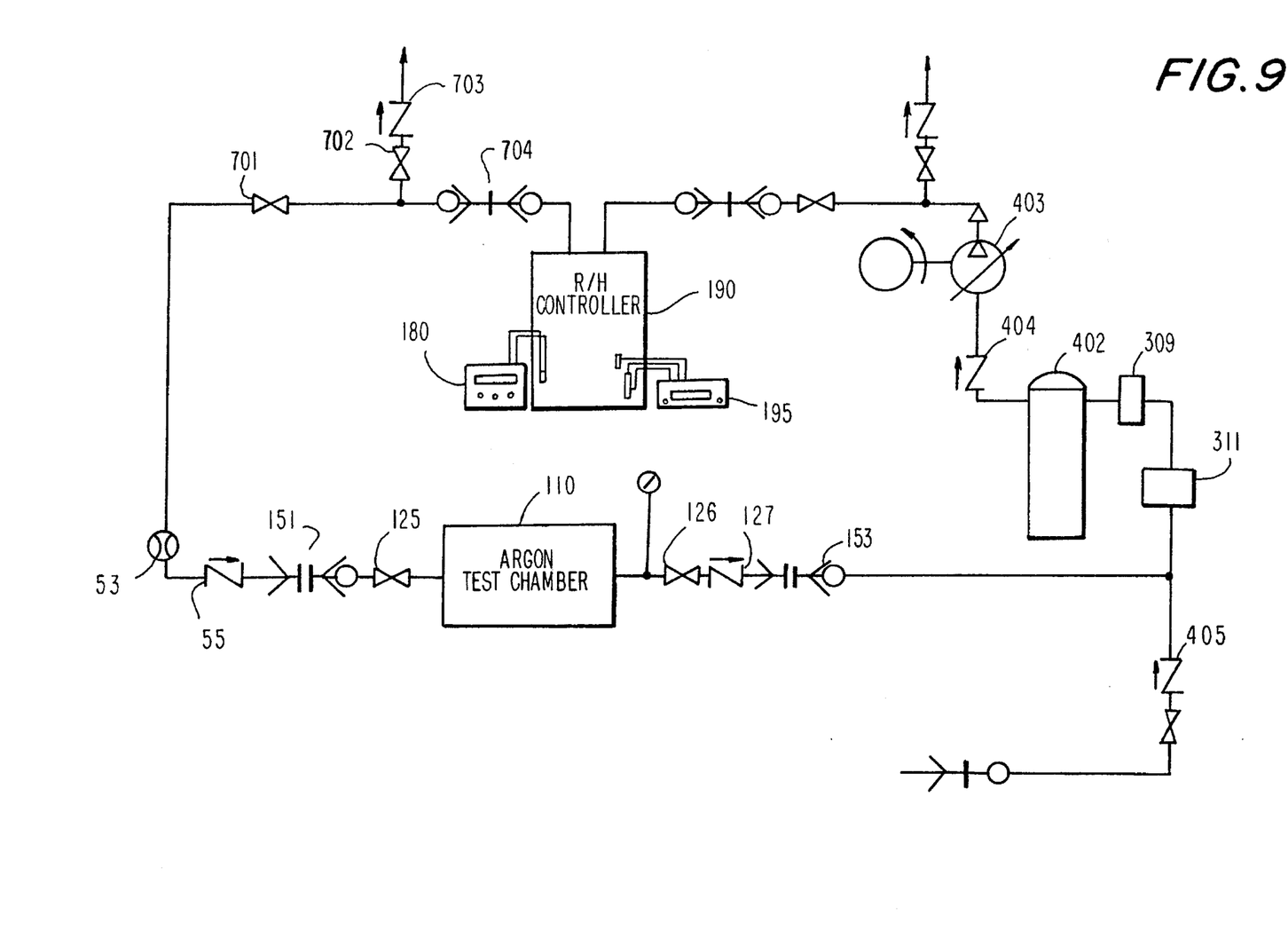
FIG. 9 depicts the system of FIG. 7 with added temperature, humidity and pH controls, in a line-purging configuration (chamber's quick-disconnect elements disconnected), for conditioning and environmental control.
Figure 10:
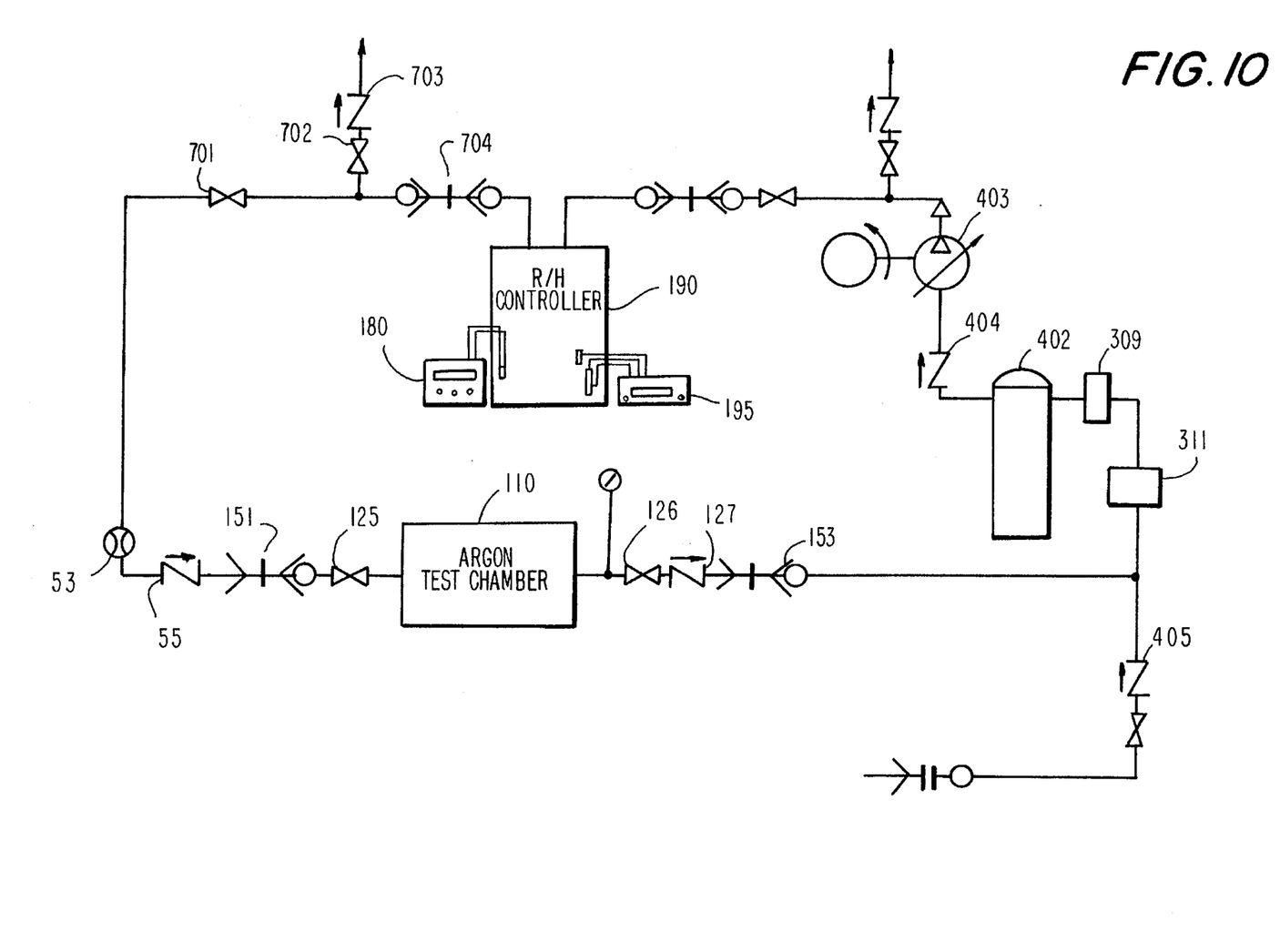
FIG. 10 depicts the treatment chamber and associated apparatus of FIG. 9 connected in a manner to provide long-term maintenance and storage of the art object contained with the treatment chamber (quick-disconnect elements reconnected to atmospheric control elements).

FIG. 9 depicts the treatment chamber connected with the apparatus of FIG. 7 in a manner which enables purging of the system (chamber's quick-disconnect elements disconnected) prior to connection to the apparatus of FIG. 10. As illustrated in FIG. 9, the apparatus includes the process chamber 110, valves 125 and 126, quick disconnect elements 151 and 153, relative humidity controller 190, temperature controller 180, pH controller 195, oxygen trap 402, ionization filter 311, pump 403, and associated check valve 403. The pressure and/or vacuum pump(s) and oxygen monitoring system are commercially available components. The inert gas inlet system utilized may be that shown in FIG. 5 discussed above.

Following treatment for a predetermined period of time, including purging of the system by utilizing the apparatus depicted in FIG. 9, the process chamber of FIG. 10 can be reattached to the system shown in FIG. 1 for the air flush and fill phase; and then connected to the apparatus depicted in FIG. 3 for measurement of parameters indicating the presence or absence of biological activity.

Assessment Of Effectiveness of Treatment

Following treatment, the process chamber and its associated control chamber are re-attached to the apparatus depicted in FIG. 1 for the air flush and fill phase. The apparatus of FIG. 1 is run in the air flush and fill mode until ambient levels of oxygen are attained in each enclosure system, as controlled by time and/or orifice size and as determined by an attached oxygen monitoring system. The process chamber and its associated control chamber are then re-attached to the system depicted in FIG. 3 for measurement of living organisms.

If respiration by-products from living organisms are still detected, then the art object and the process chamber are returned to the anoxic treatment phase (FIGS. 5 and 6), and the treatment will be repeated with an appropriate adjustment in the predetermined length-of-time (LOT) for treatment. If no respiration by-products from living organisms are detected, then the art object is deemed free from infestation and removed from the process chamber.

Supplemental Applications

The system as outlined above is adapted to perform multiple functions. Not only is it used in the primary objective of eradicating insects, fungi, algae or other undesirable biological organisms, but it may also be employed in other modes:

encapsulation of fine art or historic objects for long-term storage under inert gas conditions;

gradually drying or moistening objects;

acclimatizing or environmentally conditioning objects brought from geographical areas of different climatic conditions.

The first objective can be attained by utilization of a chamber to contain the art object within an atmosphere of an inert gas, typically argon or helium, for an extended period of time, which may be on the order of months or years. This is depicted in FIG. 10, which shows the treatment chamber 110 and associated temperature controller 180, relative humidity controller 190, pH controller 195 valves, pump 403, and meters configured in a manner to provide long-term maintenance and storage of the art object contained with the treatment chamber 110. FIG. 8 shows the apparatus which can be utilized for leak detection and may also be utilized for long term storage. As shown in FIG. 10, the quick-disconnect elements 151 and 153 are reconnected to the control elements to maintain controlled temperature, relative humidity, and pH. An ionization filter 311 can also be employed to precipitate out any spores which form during conditioning or long-term storage.

The second objective, that of gradually drying an object to be treated, is accomplished by the use of temperature controller 180, pH controller 195 and relative humidity controller 190 shown in FIG. 10. Using these elements, and based upon knowledge of the ability of the fine art object to tolerate changes in humidity and temperature, the controller can be gradually adjusted to slowly dry or moisten the object to be treated, or to acclimatize or condition an object brought from another climate. (Destruction of fungi, for example, can often be effected by gradual drying of an object.)

It will thus be seen that the overall system provides for four major capabilities which assist art conservation personnel in caring for fine art objects:

(1) the ability to non-destructively measure for the presence of living organisms in an art object;

(2) the ability to eliminate infestation by utilizing an accurately controllable system without toxic substances which may harm the object, personnel handling the object, or the environment;

(3) the capacity for long-term encapsulation and preservation of important art and historical objects under a wide variety of humidity levels for extended periods of time, at any oxygen level from ambient to anoxic in any desired gas: and (4) the provision of an accurately controllable, repeatable method to lower or raise the relative humidity in an object in order to preserve the object.

By utilizing quick-disconnect elements in conjunction with the treatment chamber and control chamber, the system can be adapted to continue to operate even while changing other elements in the system. Each element can be changed, one at a time, without interrupting gas flow until such time as it is necessary to purge that element. In addition, the system can have its own purge supply so that gas flow need not be interrupted when changing an element in the system. FIG. 2, for example, depicts the process chamber and the control chamber in a "stand-alone" configuration following the flush and fill cycle and prior to connection to activity detection apparatus. The use of quick disconnect elements as shown in FIG. 2 enables the chambers to remain sealed until further processing and/or testing is required.

It will thus be seen that the invention efficiently attains the objects set forth above, among those made apparent from the preceding description. In particular, the invention provides an anoxic insect treatment process which effectively eliminates organisms such as insects, fungi and/or microbes from fine art objects such as paintings, without causing degradation or damage to the artwork.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense. It is also to be understood that the following claims are intended to all of the generic and specific features of the invention as described herein, and all statements of the scope of the invention which, as a matter of language, might be said to fall therebetween.

Having described the invention, what is claimed as new and secured by Letters Patent is:

1. An anoxic treatment process for eliminating organisms such as insects, fungi, algae and/or microbes from an object, the process comprising the steps of:

placing the object in a sealable container, sealing the container, flushing the container of oxygen by applying an inert gas from a source of inert gas until a predetermined anoxic concentration of oxygen is attained, maintaining the object within the container under a substantially constant anoxic condition until live organisms are eliminated from the object, monitoring the object to be treated to detect biological activity within the object to be treated, and returning to the maintaining step if the monitoring step indicates biological activity within the object to be treated; and wherein the step of monitoring the object to be treated comprises the steps of activating a laser light source situated within the container, and performing a Fourier transform infrared spectroscopy measurement.

2. The process of claim 1 wherein the step of placing the object in the sealable container includes the step of utilizing a container having substantially flexible walls.

3. The process of claim 1 wherein the step of placing the object in the sealable container includes the step of utilizing a container having substantially rigid walls.

4. The process of claim 1 wherein the step of applying an inert gas includes the step of utilizing argon gas.

5. The process of claim 1 wherein the step of applying an inert gas includes the step of utilizing helium.

6. The process of claim 1 wherein the step of maintaining the object within the container under a substantially constant anoxic condition includes the step of controlling ambient temperature within the container.

7. The process of claim 1 wherein the step of maintaining the object within the container under a substantially constant anoxic condition includes the step of controlling relative humidity within the container.

8. The process of claim 1 wherein the step of maintaining the object within the container under a substantially constant anoxic condition includes the step of controlling pH of the gas within the container.

9. The process of claim 1 wherein the step of monitoring the object to be treated comprises the steps of disconnecting the container from the source of inert gas while maintaining the container in a sealed condition, and then monitoring any of the object or the gas within the chamber.

10. An anoxic treatment process for eliminating organisms such as insects, fungi, algae and/or microbes from an object, the process comprising the steps of:

placing the object in a sealable container, sealing the container, flushing the container of oxygen by applying an inert gas from a source of inert gas until a predetermined anoxic concentration of oxygen is attain, maintaining the object within the container under a substantially constant anoxic condition until live organisms are eliminated from the object, monitoring the object to be treated to detect biological activity within the object to be treated, and wherein the step of monitoring the object to be treated comprises the further steps of subsequent to separating the container from the source of inert gas, purging the inert gas from the container utilizing a source of purge gas;

filling a second container with purge gas from the same source of purge gas; and comparing the gas within the first container and the gas within the second container.

11. The process of claim 10 wherein monitoring to detect biological activity includes the step of monitoring by-products of metabolic processes.

12. The process of claim 11 wherein the step of monitoring by-products includes the step of monitoring any of carbon dioxide, methane, or other respired gases from organisms.

13. The process of claim 12 wherein the step of monitoring by-products includes the step of performing Fourier transform infrared spectroscopy measurements.

14. The process of claim 12 wherein the step of monitoring by-products includes the step of employing a gas chromatograph.

15. The process of claim 1 wherein the step of detecting biological activity includes the step of employing bioluminescent agents.

16. The process of claim 1 wherein the step of monitoring comprises the step of utilizing a solid-state sensor, cermet sensor, or other bio-sensor.

17. An anoxic treatment apparatus for eliminating organisms such as insects, fungi, algae and/or microbes from an object, the apparatus comprising:

a sealable container for containing the object, a source of inert gas coupled to the sealable container to provide a predetermined anoxic concentration of oxygen within the container, and to maintain the object within the container under a substantially constant anoxic condition until live organisms are eliminated from the object, and monitoring elements constructed and arranged to detect biological activity within the object to be treated while the object is within the sealable container, said monitoring elements providing a signal indicative of a requirement to continue maintaining the object within the container under the substantially constant anoxic condition, said signal being provided upon detection of the presence of biological activity within the object to be treated, wherein said monitoring elements comprise a laser light source situated within the container, and measurement means constructed and arranged to perform a Fourier Transform Infrared Spectory measurement.

* * * * *